United States Patent [19]

Nagy et al.

[11] Patent Number: 6,008,394

[45] Date of Patent: Dec. 28, 1999

[54] SULFONYL CATALYSTS AND METHOD OF USING THE SAME

[75] Inventors: Sandor Nagy, Grand Island; John Tyrell, Williamsville, both of N.Y.; Bradley P. Etherton, Houston, Tex.

[73] Assignee: ARCO Chemicals Technology, L.P., Greenville, Del.

[21] Appl. No.: 09/130,701

[22] Filed: Aug. 7, 1998

[51] Int. Cl.⁶ .......................... C07F 17/00; C08F 4/643; C08F 4/602
[52] U.S. Cl. ..................... 556/51; 556/1; 556/7; 556/43; 556/46; 556/58; 556/136; 556/143; 556/144; 526/127; 526/160; 526/352; 526/943; 502/103; 502/117; 502/155; 502/120
[58] Field of Search .................. 556/43, 46, 51, 556/53, 58, 136, 143, 144, 7, 1; 502/103, 117, 155, 120; 526/127, 160, 943, 352

[56] References Cited

PUBLICATIONS

Nishibayashi et al., J. Org. Chem., vol. 61, No. 3, pp. 1172–1174, Feb. 9, 1996.

*Primary Examiner*—Porfirio Nazario-Gonzalez

*Attorney, Agent, or Firm*—Jonathan L. Schuchardt

[57] ABSTRACT

A novel metallocene catalyst for the polymerization of olefin (co)polymers is of the general formula:

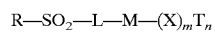

wherein,

M is a metal selected from Groups 3–10;

T is a polymerization-stable anionic ancillary ligand;

m+n is the valency of M minus 1;

R is a $C_1$–$C_{20}$ alkyl group, a $C_6$–$C_{20}$ aryl ring or a $C_6$–$C_{20}$ alkaryl or aralkyl group, optionally substituted with a halogen or an alkoxy group up to 10 carbon atoms;

X is a halogen, alkoxy from $C_1$ to $C_{20}$, siloxy from $C_1$ to $C_{20}$, $N(R)_2$, a hydrocarbyl group containing up to about 12 carbon atoms, hydrogen or another univalent anionic ligand, or mixtures thereof;

L is T as defined above with the proviso that one of the sites available for substitution is the attachment site of the sulfonyl group; and wherein L and T may be bridged.

21 Claims, No Drawings

SULFONYL CATALYSTS AND METHOD OF USING THE SAME

FIELD OF THE INVENTION

This invention relates to a novel metallocene catalyst system comprising a polymerization catalyst having at least one polymerization-stable anionic ancillary ligand derivatized with a sulfonyl group. The invention further relates to a method of preparation of the catalyst and a method of using the same.

BACKGROUND OF THE INVENTION

Historically, polyolefins have been made with conventional Ziegler catalyst systems. Such catalysts typically consist of transition metal-containing compounds and one or more organometallic compounds. For example, polyethylene has been made using such Ziegler catalysts as titanium trichloride and diethylaluminum chloride, as well as a mixture of titanium tetrachloride, vanadium oxytrichloride, and triethylaluminum.

While these catalysts are inexpensive, they exhibit low activity and therefore must be used at high concentrations. As a result, it is sometimes necessary to remove catalyst residues from the polymer, which adds to production costs. Neutralizing agents and stabilizers must be added to the polymer to overcome the deleterious effects of the catalyst residues. Failure to remove catalyst residues leads to polymers having a yellow or grey color and poor ultraviolet and long term stability. Additionally, for example, chloride-containing residues can cause corrosion in polymer processing equipment.

Furthermore, Ziegler catalysts produce polymers having a broad molecular weight distribution which is undesirable for some applications such as injection molding. They are also poor at incorporating α-olefin co-monomers. Poor co-monomer incorporation makes it difficult to control the polymer density. Large quantities of excess co-monomer may be required to achieve a certain density and many higher α-olefins, such as 1-octene, may be incorporated at only very low levels, if at all.

Although significant improvements in Ziegler catalyst systems have occurred since their initial discovery, they lately have been substantially replaced with "single-site," in particular, metallocene, catalyst systems. A traditional metallocene catalyst typically consists of a transition metal compound which has one or more cyclopentadienyl ring ligands bound in an $\eta^5$ fashion. The cyclopentadienyl ring ligands are polymerization-stable; that is, they remain bound to the metal during the course of the polymerization process. They produce polymers of high molecular weight and display narrow molecular weight distributions, because the cyclopentadienyl ligands deter formation of secondary polymerizing species. These catalysts also incorporate α-olefin co-monomers well. However, at higher temperatures traditional metallocene catalysts tend to produce lower molecular weight polymers. They are particularly useful for gas phase and slurry polymerizations of ethylene, which are conducted at about 80° C. to about 95 ° C., but are less useful in solution polymerizations of ethylene, at about 150° C. to about 250° C. Additionally, gas phase and slurry polymerizations using supported metallocene catalysts can suffer from sheeting and equipment fouling problems.

Recently, catalysts have been discovered wherein one or more of the cyclopentadienyl ring ligands associated with the traditional metallocene have been replaced by other polymerization-stable anionic ancillary ligands. These may be ligands which are isolobal to cyclopentadienyl; that is, the frontier molecular orbitals—the highest occupied and lowest unoccupied molecular orbitals—of the ligand and those of the cyclopentadienyl ligand are similar. These isolobal ligands may include tris(pyrazolyl)borates, pentadienyl groups, phospholes, and carbollides.

In particular, U.S. Pat. No. 5,554,775, incorporated herein by reference, discloses catalysts wherein one or both cyclopentadienyl moieties are replaced by a borabenzene moiety including boranaphthalene and boraphenanthrene. Further, U.S. Pat. No. 5,539,124, incorporated herein by reference, discloses catalysts in which one or both cyclopentadienyl moieties have been replaced by a nitrogen-containing heteroaromatic compound containing a pyrrolyl ring, i.e., an azametallocene, variously substituted. The heteroaromatics disclosed in the latter patent include, e.g., indolyl, isoindolyl, and carbazolyl, and other homologous heteroaromatic moieties. The foregoing heteroaromatic catalysts may be referred to generally as heterometallocenes. In addition, PCT International Application WO 96/34021 discloses azaborolinyl heterometallocenes wherein at least one aromatic ring is complexed with a transition metal. Such rings include both a boron atom and a nitrogen atom. These specifically will be referred to as, e.g., azaborolines and the catalysts derived therefrom as azaborolinyl catalysts. The latter catalysts also fall into the general group referred to as heterometallocenes. The foregoing metallocene and heterometallocene catalysts have been developed to include bulky ligands attached to the aromatic moieties. Increased control of the polymerization process may therefore be provided.

Because supported catalysts are more stable, may produce higher molecular weight polymers, and may produce useful changes in the morphology of the polymer, metallocene catalysts are often used in conjunction with a support, such as silica gel.

For the purposes of the present disclosure, it is to be understood that when the term "metallocene" is used, both traditional metallocenes and heterometallocenes such as those disclosed in the above referenced U.S. patents and applications, including those containing bulky ligands, are contemplated to fall within the scope of the term. Thus, "metallocene" is considered to be a generic term for all such transition metal-bonded aromatic organic polymerization catalysts. Likewise, it is to be understood that when the term "single-site" catalyst is used, both metallocenes as well as other metal complexes containing polymerization-stable ancillary ligands are contemplated to fall within the scope of the term.

SUMMARY OF THE INVENTION

The invention relates to a novel metallocene catalyst system comprising a polymerization catalyst which contains at least one polymerization-stable anionic ancillary ligand derivatized with a sulfonyl group and a Group 3–10 metal. The sulfonyl group is attached to the ancillary ligand through a conventional sigma bond and is also attached to an alkyl or aryl group, optionally substituted with a halogen or an alkoxy group up to 10 carbon atoms.

The sulfonyl group presumably stabilizes the active metal center to achieve high productivity, good comonomer incorporation, and narrow molecular weight distribution characteristic of the single site catalyst.

DESCRIPTION OF THE PREFERRED EMBODIMENTS

A novel metallocene catalyst for the polymerization of olefin (co)polymers is of the general formula:

$$R-SO_2-L-M(X)_m T_n$$

wherein,

M is a metal selected from Groups 3–10, preferably Groups 3–7, more preferably Groups 4–6, most preferably Group 4, of the Periodic Table or a metal from the lanthanide or actinide series;

T is a polymerization-stable anionic ancillary ligand;

n is either 0 or 1;

m+n is the valency of M minus 1;

R is a $C_1$ to $C_{20}$ alkyl group, a $C_6$ to $C_{20}$ aryl ring or a $C_6$ to $C_{20}$ alkaryl or aralkyl group, optionally substituted with a halogen or an alkoxy group containing up to 10 carbon atoms;

X is a halogen (preferably —Cl or —Br), alkoxy from $C_1$ to $C_{20}$, siloxy from $C_1$ to $C_{20}$, dialkylamido, $(N(R_1)_2)$, a hydrocarbyl group containing up to about 12 carbon atoms, hydrogen or another univalent anionic ligand, or mixtures thereof; preferably X is chloride, methyl, benzyl, methoxy, ethoxy, dimethylamido, or siloxy $(R_1)_3SiO—$, where $R_1$ is alkyl from $C_1$ to $C_{20}$; and L is T as defined above with the proviso that one of the sites available for substitution is the attachment site of the sulfonyl group; and wherein L and T may be bridged.

The transition metal of the catalyst of the invention may be any Group 3 to 10 metal or a metal from the lanthanide or actinide series. In a preferred embodiment, the catalyst contains a Group 4, 5, or 6 transition metal. In a particularly preferred embodiment, the catalyst contains a Group 4 metal, particularly zirconium, titanium or hafnium.

T may be cyclopentadienyl, boraaryl, pyrrolyl, azaborolinyl, pyridinyl, quinolinyl, or homologous ligands. Typical of the T ligands in the catalyst of the invention are the mono- or bi-cyclopentadienyl or substituted cyclopentadienyl radicals, especially those of the formulae:

$$(C_5R^1_w)_f R^2_s (C_5R^1_w) \quad (I)$$

and $$R^2_s(C_5R^1_w)_2 \quad (II)$$

wherein, ($C_5R^1_w$) is a cyclopentadienyl or substituted cyclopentadienyl; each $R^1$ is the same or different and is hydrogen or a hydrocarbyl radical such as alkyl, alkenyl, aryl, alkaryl or aralkyl radical containing from 1 to 20 carbon atoms of which two carbon atoms may be joined together to form a C4 to C6 ring;

$R^2$ is a $C_1$–$C_{20}$ alkylene radical, a dialkyl germanium or dialkyl silicon [such as silyl or a radical of the formula —Si($R_5$)$_2$ wherein each $R_5$ is H, a $C_1$–$C_{10}$ (preferably a $C_1$–$C_4$) alkyl group, an aryl such as benzyl or phenyl or a benzyl or phenyl group substituted with one or more $C_1$–$C_4$ alkyl groups] or an alkyl phosphine or amine radical bridging two ($C_5R^1_w$) rings;

s is 0 or 1;

f is 0, 1 or 2 provided that when f is 0, s is 0;

w is 4, when s is 1;

w is 5, when s is 0.

Particularly good results are obtained where the cyclopentadienyl ring is of the structure:

(III)

where each substituent group, $R_2$, is independently selected from a $C_1$ to $C_{20}$ hydrocarbyl group and r is a number from 0 to 5. In the case in which two $R_2$ groups are adjacent, they can be joined to produce a ring which is fused to the cyclopentadienyl ring. Examples of alkyl substituted cyclopentadienyl rings include n-butylcyclopentadienyl, methylcyclopentadienyl and pentamethylcyclopentadienyl. Examples of fused cyclopentadienyl ring ligands include indenyl, tetrahydroindenyl, fluorenyl and 2-methylindenyl.

The ligand T for use in the olefin polymerization catalyst for the invention may further contain 4 to 30 carbon atoms and may contain a fused ring, one of which is a pyrrolyl ring. Included within this group are heterocyclic radicals of the formula:

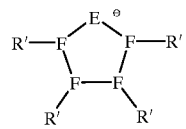
(IV)

wherein,

R' is independently hydrogen or $R^{80}$ or with F forms a $C_4$ to $C_{10}$ fused ring;

each $R^{80}$ is independently selected from hydrogen, a $C_1$ to $C_{20}$, preferably a $C_1$ to $C_6$, aliphatic or cycloaliphatic radical; a $C_6$–$C_{30}$, preferably a $C_6$–$C_{15}$, aryl radical, or a $C_7$–$C_{30}$, preferably $C_7$–$C_{15}$, aralkyl or alkaryl radical;

E independently represents a trivalent atom selected from nitrogen, phosphorus, arsenic, antimony and bismuth; and F is independently selected from carbon and E.

Exemplary compounds include those wherein R' is —H or a $C_1$ to $C_6$ alkyl group or $C_6$ to $C_{10}$ aryl group. Preferred compounds include 2-methylpyrrolyl, 3-methylpyrrolyl, 2,5-dimethylpyrrolyl, 2,5-di-tert-butylpyrrolyl, aryl substituted pyrrolyl rings such as 2-phenylpyrrolyl, 2,5-diphenylpyrrolyl, indolyl and alkyl substituted indolyls of the formula:

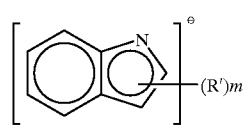
(V)

such as 2-methylindolyl, 2-tert-butylindolyl, 3-n-butylindolyl, 7-methylindolyl, and 4,7-dimethylindolyl and carbazolyl and alkyl substituted carbazolyls of the formula:

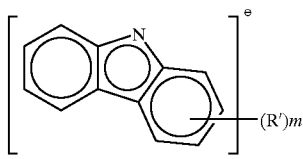

where m=0 to 8 and $R^1$ is as defined above. The alkyl and aryl substituents on the pyrrolyl ring-containing ligand are not on the nitrogen atom in the ring but are on the carbon atoms of the ring.

Additional examples of ring structures include those π-ligands that comprise compounds such as:

1-Phospha-2,3,4,5-tetramethylcyclopentadienyl,
1-Phospha-3,4-diphenylcyclopentadienyl;
1-Phosphaindenyl,
1-Phospha-3-methoxycyclopentadienyl,
1,3-Diphospha-4,5-diphenylcyclopentadienyl,
1,2,4-Triphospha-3,5-diphenylcyclopentadienyl,
1,2,3,4-Tetraphospha-5-phenylcyclopentadienyl,
Pentaphosphacyclopentadienyl,
1-Phospha-3-benzoyloxycyclopentadienyl,
Imidazolyl,
Pyrazolyl,
1,2,3-triazolyl,
1,2,4-triazolyl,
Tetrazolyl, and
Pentazolyl.

Still further, the ligand T may be of the formula:

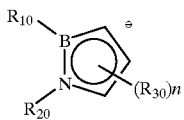

wherein, $R_{10}$ is independently selected from $R_{25}$, alkaryl from $C_6$ to $C_{12}$, aralkyl from $C_6$ to $C_{12}$, hydrogen, or $Si(R_{25})_3$, $R_{25}$ is alkyl from $C_1$ to $C_{12}$ or aryl from $C_6$ to $C_{12}$, $R_{20}$ is $R_{10}$, halogen, or $COR_{25}$, $R_{30}$ is $R_{20}$, $OR_{25}$, $N(R_{25})_2$, $SR_{25}$, or a fused ring system and n is a number from 0 to 3.

The $R_{25}$ group is preferably alkyl from $C_1$ to $C_4$, the $R_{10}$ group is preferably $C_1$ to $C_6$ alkyl or —$Si(R_{25})_3$ and the $R_{30}$ group is preferably hydrogen or methyl. Examples of fused ring structures that can be used include:

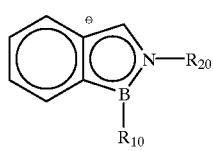

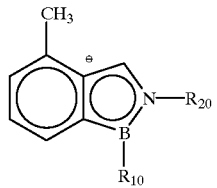

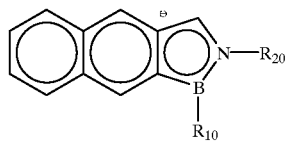

The T ligand may further be a boratabenzene ligand. A boratabenzene ring has the structure:

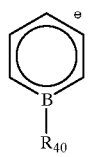

where $R_{40}$ can be hydrogen, $N(R_{50})_2$, $OR_{50}$, or $R_{50}$, where each $R_{50}$ is independently selected from alkyl from $C_1$ to $C_{10}$, aryl from $C_6$ to $C_{15}$, alkaryl from $C_7$ to $C_{15}$, and aralkyl from $C_7$ to $C_{15}$. The $R_{40}$ group is preferably —$N(R_{50})_2$, methyl, or phenyl and, if $R_{40}$ is —$N(R_{50})_2$, then the $R_{50}$ in —$N(R_{50})_2$ is preferably methyl.

Exemplary of the boratabenzene ligands include:

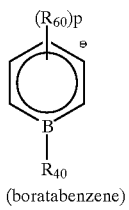
(boratabenzene)

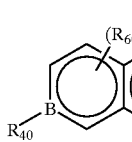
(boratanaphthalene)

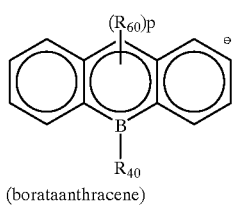
(boratanthracene)

(XV)

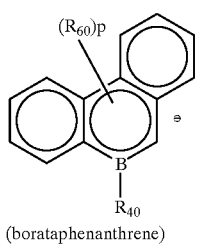
(borataphenanthrene)

where "p" is 0 to the maximum number of substitutable positions, and is preferably 0 or 1. Each $R_{60}$ is independently selected from halogen, alkoxy from $C_1$ to $C_{10}$, silyl (—Si$(R_{50})_3$) and $R_{50}$. Particularly preferred boratabenzene ligands are 1-methyl-1- boratabenzene, 2-phenyl-2-boratanaphthalene, 9-mesityl-9- borataanthracene and 1-methyl-2-trimethylsilyl-1-boratabenzene.

Still, T may be selected from the radicals:

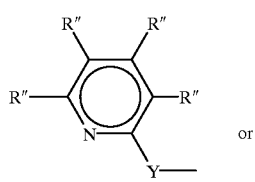
(XVI)

or

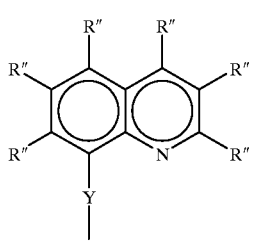
(XVII)

wherein R" is independently selected from $R^{85}$, $C_1$ to $C_6$ alkoxy, $C_7$ to $C_{20}$ alkaryl, $C_7$ to $C_{20}$ aralkyl, halogen, or $CF_3$; each $R^{85}$ is independently selected from hydrogen, $C_1$ to $C_6$ alkyl, or $C_6$ to $C_{14}$ aryl; and Y is O, S, $NR^{65}$, or $PR^{65}$;

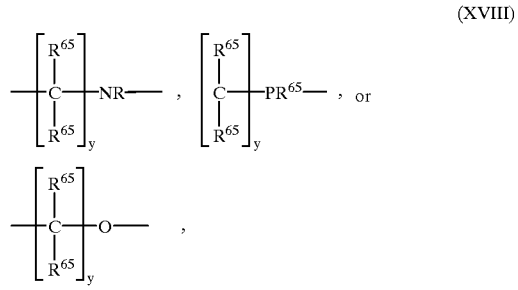
(XVIII)

wherein $R^{65}$ is a $C_1$ to $C_6$ alkyl and y is 1 to 4.

L can be any of the aforementioned ligands defined for T with the proviso that one of the substitution sites of the ligand is attached to the sulfonyl group.

Groups that can be used to bridge two ligands include methylene, ethylene, 1,2-phenylene, dimethylsilyl, diphenylsilyl, diethylsilyl, and methylphenylsilyl. Normally, only a single bridge is used in a catalyst. It is believed that bridging the ligand changes the geometry around the catalytically active transition metal and improves catalyst activity and other properties, such as comonomer incorporation and thermal stability.

The catalysts of this invention can be prepared in a variety of ways. Typically, in the first step in producing the catalyst, an alkali metal salt of the L substituent is reacted with a sulfonyl halide, such as benzenesulfonyl chloride or a halogenated alkylsulfonyl chloride. For example, sodium (1-methylborabenzene) could be reacted with phenyl sulfonyl chloride to produce 1-methyl-2-phenylsulfonyl boraben-zene. Sodium chloride would be filtered off. Stoichiometric quantities are typically used. The reaction is preferably performed by dissolving the reactants in an organic solvent which does not have an active proton such as tetrahydrofuran, anisole, or ethyl ether. The solution should be as concentrated as possible to reduce the amount of solvent that must be handled. The reaction can occur at room temperature, but lower temperatures may be desirable in order to reduce the amount of by-products.

The final polymerization stable anionic ancillary ligand is then prepared by treating the reaction product of L and the sulfonyl chloride compound with a strong base such as a n-butyl lithium or lithium di(isopropyl)amide (LDA). This is then reacted with a transition metal complex with Y. For example, a mixture of 1-methyl-2-phenylsulfonylborabenzene and LDA would be reacted with (1-methylborabenzene) zirconium trichloride. This would produce (1-methyl-2-phenylsulfonylborabenzene) (1-methylborabenzene) zirconium dichloride. Stoichiometric quantities of these reactants are used typically used. The byproducts are removed by filtration, the solvent is evaporated, and the metal ligand catalyst is collected.

The catalysts of this invention are believed to be single site catalysts since they produce polymers with a very narrow molecular weight distribution. The ratio of weight average molecular weight to number average molecular weight is generally close to 2.

The catalyst of the invention is normally used in conjunction with a co-catalyst. Representative co-catalysts include alumoxanes and aluminum alkyls of the formula $Al(R^7)_3$ where $R^7$ independently denotes a $C_1$–$C_8$ alkyl group, hydrogen or halogen. Exemplary of the latter of such co-catalysts are triethylaluminum, trimethylaluminum and tri-isobutylaluminum. The alumoxanes are polymeric aluminum compounds typically represented by the cyclic formulae $(R^8$—Al—O$)_s$ and the linear formula $R^8(R^8$—Al—O$)_s AlR^8$ wherein $R^8$ is a $C_1$–$C_5$ alkyl group such as methyl, ethyl, propyl, butyl and pentyl and s is an integer from 1 to about 20. Preferably, $R^8$ is methyl and s is about 4 to about 10. Representative but non-exhaustive examples of alumoxane co-catalysts are (poly)methylalumoxane (MAO), ethylalumoxane and diisobutylalumoxane as well as aluminum alkyls such as triethylaluminum, trimethylaluminum, and tri-isobutylaluminum. Examples of suitable co-catalysts further include mixtures of MAO with the above-referenced aluminum alkyls. The preferred co-catalyst is MAO as it results in high catalyst activity, good comonomer incorporation, and a polymer having a narrower molecular weight distribution.

The co-catalyst can further be a substituted or unsubstituted tri-alkyl or tri-aryl boron derivative, such as tris (perfluoro)boron as well as ionic compounds such as tri (n-butyl) ammonium tetrakis (pentafluorophenyl) boron or trityl tetrakis(perfluorophenyl)boron which ionize the neutral metallocene compound. Such ionizing compounds may contain either an active proton, or a cation associated with, but not coordinated or only loosely coordinated to, the remaining ion of the ionizing compound. See, for instance, U.S. Pat. Nos. 5,153,157; 5,198,401; and 5,241,025, all of which are herein incorporated by reference.

It is preferable to dissolve the metal compound in a solvent in which the co-catalyst is also soluble. For example, if methylalumoxane (MAO) is the co-catalyst, then toluene, xylene, benzene, or ethyl benzene could be used as the solvent. It is often preferable not to premix the catalyst and the co-catalyst as this may result in lower catalyst activity. Rather, the catalyst and co-catalyst are preferably injected separately into a reactor containing the monomer to be polymerized. And, preferably, the co-catalyst is injected first. The amount of cocatalyst used with the transition metal compound can be in a molar ratio ranging from about 1:1 to about 15,000:1.

The catalyst and co-catalyst can also be used on a support such as silica gel, alumina, magnesia, or titania. Supports are not generally preferred as they leave additional contaminants in the polymer. However, a support may be required depending upon the process being utilized. For example, a support is generally needed in gas phase polymerization processes and slurry polymerization processes in order to control the particle size of the polymer being produced and in order to prevent fouling of the reactor walls. In order to use a support, the catalyst is dissolved in a solvent and is deposited onto the support material by evaporating the solvent. The cocatalyst can also be deposited on the support or it can be introduced into the reactor separately from the supported catalyst.

Once the catalyst has been prepared it should be used as promptly as possible as it may lose some activity during storage. Storage of the catalyst should be at a low temperature, such as −100° C. to 20° C. The catalyst is used in a conventional manner in the polymerization of unsaturated olefinic monomers.

The catalyst is also useful for copolymerizing mixtures of ethylene with unsaturated monomers such as 1-butene, 1-hexene, 1-octene, and the like; mixtures of ethylene and di-olefins such as 1,3-butadiene, 1,4-hexadiene, 1,5-hexadiene, and the like; and mixtures of ethylene and unsaturated comonomers such as norbomadiene, ethylidene norbomene, vinyl norbomene, and the like.

While unsaturated monomers such as styrene can be polymerized using the catalysts of this invention, it is particularly useful for polymerizing α-olefins such as propylene, 1-butene, 1-hexene, 1-octene, and especially ethylene.

The catalysts of this invention can be utilized in a variety of different polymerization processes. They can be utilized in a liquid phase polymerization process (slurry, solution, suspension, bulk phase, or a combination of these), in a high pressure fluid phase, or in a gas phase polymerization process. The processes can be used in series or as individual single processes. The pressure in the polymerization reaction zones can range from about 15 psia to about 50,000 psia and the temperature can range from about −100° C. to about 300° C.

The following examples further illustrate this invention.

EXAMPLES

Example 1

This example describes the synthesis of (sulfonylphenyl tetramethyl cyclopentadienyl) cyclopentadienyl zirconium dichloride of the formula:

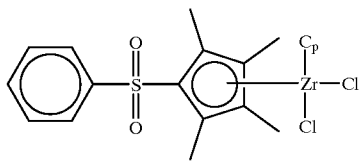

where $C_p$ is cyclopentadienyl.

To 1.28 grams (0.01 mole) lithium tetramethylcyclopentadiene stirring under argon atmosphere with 50 ml of dry tetrahydrofuran at −78° C. was added 1.28 ml. (0.01 mole) benzenesulfonyl chloride via syringe. The mixture was stirred for 1 hour. To the mixture was added 6.25 ml of 1.6 M n-butyl lithium in hexane (0.01 mole) and 2.63 grams (0.01 mole) cyclopentadienylzirconium trichloride. Stirring was continued and the reaction mixture was allowed to slowly warm to room temperature. After stirring at room temperature for 16 hours, the yellow solution was concentrated with vacuum to obtain a yellow gummy solid which turned purple upon exposure to air. To this yellow gummy solid, dry toluene was added, the mixture was filtered and volatiles removed from the filtrate to obtain the product catalyst as an orange gummy solid.

Example 2

This example describes the preparation of (trifluoromethylsulfonyl tetramethyl cyclopentadienyl) cyclopentadienylzirconium dichloride of the formula:

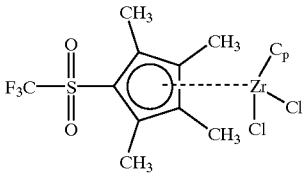

To 1.02 grams (0.008 mole) lithium tetramethylcyclopentadiene stirring under argon atmosphere with 30 ml of dry tetrahydrofuran at −78° C. was added 0.85 ml. (0.008 mole) trifluoromethylsulfonyl chloride via syringe. The mixture was stirred for 3 hours. To the mixture was added 5 ml. of 1.6M n-butyl lithium in hexane (0.008 mole) and 2.1 grams (0.008 mole) cyclopentadienylzirconium trichloride. Stirring was continued and the reaction mixture was allowed to slowly warm to room temperature. After stirring at room temperature for 16 hours, the pale orange solution was concentrated with vacuum. To this material, 20 ml dry toluene was added, the toluene solution removed by cannula and the toluene removed by vacuum to obtain the product catalyst.

Examples 3–9

Ethylene was polymerized using the catalysts of Examples 1 and 2. Examples 3 through Example 7 used the catalyst prepared in Example 1 and Examples 8 and 9 used the catalyst prepared in Example 2.

The polymerization was conducted in a stirred 1.7 liter stainless steel autoclave at 80° C. and 110° C. Dry, oxygen-free toluene (840 ml) was charged to the dry, oxygen-free reactor. 10% MAO in toluene (obtained from Ethyl Corporation and used without additional purification) was added with a syringe. A solution of catalyst was prepared by dissolving 0.100 grams of product in 100 ml of toluene and the desired amount was added to the catalyst injector. The reactor was then heated to the desired temperature and sufficient ethylene was added to bring the reactor pressure to 150 psig. The reactor was allowed to equilibrate at the reaction temperature and pressure. The catalyst was injected. Ethylene flowed into the reactor in order to keep the pressure constant as polyethylene was injected into the reactor. At the end of one hour the ethylene flow was stopped and the reactor was rapidly cooled to room temperature. The polymer was filtered from the toluene, dried in a vacuum oven, and weighed.

In the following, Exhibit 1 lists the polymerization conditions and Exhibit 2 shows the results of the polymerizations. The melt index of the polymer was measured according to ASTM D-1238, Condition E and Condition F. MI is the melt index measured with a 2.16 Kg weight (Condition E). HLMI is the melt index measured with a 21.6 kg weight (Condition F). The melt flow ratio (MFR) is defined as the ratio of HLMI and of MI and is a measure of molecular weight distribution. A MFR below 25 indicates narrow molecular weight distribution and is likely to demonstrate the improved properties characteristic of a single site catalyst or metallocene. Typically a Ziegler-Natta catclyst yields polymer with a MFR of around 35. The polymer density was measured according to ASTM D-1505.

Exhibit 1. Polymerization Conditions

| Example | Reactor Temp. (° C.) | Time, min | Hydrogen delta P, psi | Comonomer | Catalyst (mmoles) | Co-Catalyst | Al/M (atomic) |
|---|---|---|---|---|---|---|---|
| 3 | 80 | 60 | 0 | None | 0.0052 | MAO | 1720 |
| 4 | 110 | 60 | 0 | None | 0.0052 | MAO | 1720 |
| 5 | 110 | 60 | 0 | None | 0.0052 | MAO | 2590 |
| 6 | 110 | 30 | 10 | None | 0.0052 | MAO | 1724 |
| 7 | 110 | 30 | 10 | Butene, 15 ml | 0.0052 | MAO | 1720 |
| 8 | 80 | 60 | 0 | None | 0.0042 | MAO | 2153 |
| 9 | 80 | 60 | 0 | None | 0.0042 | MAO | 3230 |

Exhibit 2. Polymerization Results

| Example | Wt. PE (g) | Catalyst Activity kg/g/hr (kg/g Zr/hr) | MI dg/min | HLMI dg/min | MFR | Density (g/ml) |
|---|---|---|---|---|---|---|
| 3 | 41.0 | 86.1 | 0.090 | 0.9429 | 10.45 | — |
| 4 | 68.8 | 144 | 1.14 | 25.57 | 22.41 | 0.9603 |
| 5 | 71.7 | 151 | 1.33 | 33.0 | 24.78 | 0.9641 |
| 6 | 105.5 | 443 | 20.4 | — | — | 0.9713 |
| 7 | 119.2 | 500 | 61.1 | — | — | 0.9540 |
| 8 | 134 | 35.2 | 0.72 | — | — | — |
| 9 | 24.6 | 65.4 | 0.033 | 0.873 | 26.5 | — |

What is claimed is:

1. A catalyst comprising a compound of the general formula:

$$R-SO_2-L-M-(X)_mT_n$$

wherein

M is a metal selected from Groups 3–7 of the Periodic Table;

T is a polymerization-stable anionic ancillary ligand;

n is either 0 or 1;

m+n is the valency of M minus 1;

R is a $C_1$–$C_{20}$ alkyl group, a $C_6$–$C_{20}$ aryl ring or a $C_6$–$C_{20}$ alkaryl or aralkyl group, optionally substituted with a halogen or an alkoxy group having up to 10 carbon atoms;

X is a halogen, alkoxy from $C_1$ to $C_{20}$, siloxy from $C_1$ to $C_{20}$, dialkylamido, a hydrocarbyl group containing up to about 12 carbon atoms, hydrogen or another univalent anionic ligand, or mixtures thereof; and L is T as defined above with the proviso that one of the sites available for substitution is the attachment site of the sulfonyl group; and wherein L and T may be bridged.

2. The catalyst of claim 1, wherein L and/or Y are independently selected from a substituted or unsubstituted cyclopentadienyl, boraaryl, pyrrolyl, azaborolinyl, quinolinyl, or pyridinyl group.

3. The catalyst of claim 1, wherein M is a metal of Groups 4 to 6.

4. The catalyst of claim 1, wherein M is a Group 4 metal.

5. The catalyst of claim 4, wherein M is titanium or zirconium.

6. The catalyst of claim 1, wherein X is chlorine or bromine.

7. The catalyst of claim 1 having the structure:

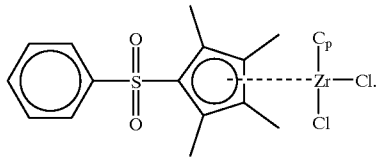

8. The catalyst of claim 1 having the structure:

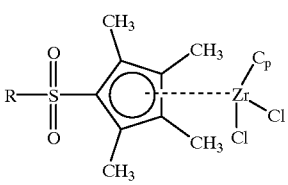

wherein R is a $C_1$ to $C_3$ alkyl or a halogenated derivative thereof.

9. A catalyst system comprising a cocatalyst and a compound of the general formula:

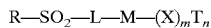

wherein

- M is a metal selected from Groups 3–10 of the Periodic Table;
- T is a polymerization-stable anionic ancillary ligand;
- n is either 0 or 1;
- m+n is the valency of M minus 1;
- R is a $C_1$–$C_{20}$ alkyl group, a $C_6$–$C_{20}$ aryl ring or a $C_6$–$C_{20}$ alkaryl or aralkyl group, optionally substituted with a halogen or an alkoxy group having up to 10 carbon atoms;
- X is a halogen, alkoxy from $C_1$ to $C_{20}$, siloxy from $C_1$ to $C_{20}$, dialkylamido, a hydrocarbyl group containing up to about 12 carbon atoms, hydrogen, or another univalent anionic ligand, or mixtures thereof; and
- L is T as defined above with the proviso that one of the sites available for substitution is the attachment site of the sulfonyl group; and wherein L and T may be bridged.

10. The catalyst system of claim 9, wherein the cocatalyst is an aluminoxane.

11. A supported catalyst system of claim 9.

12. The catalyst system of claim 9, wherein the cocatalyst is a trialkyl or triaryl boron derivative.

13. The catalyst system of claim 9, wherein the cocatalyst is a neutral boron containing compound or an ionic borate.

14. A method of polymerizing an unsaturated olefinic monomer comprising contacting said monomer with the catalyst according to claim 1.

15. The method of claim 14, wherein the olefinic monomer is ethylene.

16. The method of claim 14, wherein the olefinic monomer is ethylene and a second alpha-olefin.

17. A method of polymerizing an unsaturated olefinic monomer comprising contacting said monomer with the catalyst system of claim 9.

18. The method of claim 17, wherein the olefinic monomer is ethylene or ethylene and a second alpha-olefin.

19. A method of polymerizing an unsaturated olefinic monomer comprising contacting said monomer with the catalyst of claim 7.

20. A method of polymerizing an unsaturated olefinic monomer comprising contacting said monomer with the catalyst of claim 8.

21. A method of polymerizing an unsaturated olefin monomer comprising contacting said monomer with a catalyst of the formula:

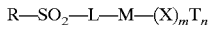

wherein

- M is Ti or Zr;
- R is a $C_1$–$C_3$ alkyl, haloalkyl or aryl group;
- X is Cl;
- L is a substituted or unsubstituted cyclopentadienyl;
- T is L;
- n is either 0 or 1; and
- m+n is the valency of M minus 1.

* * * * *